United States Patent [19]

Hermeling et al.

[11] Patent Number: 5,464,508
[45] Date of Patent: Nov. 7, 1995

[54] PREPARATION OF 4-DIALKOXYMETHYLPYRAZOLES

[75] Inventors: Dieter Hermeling, Frankenthal; Hartmann Koenig, Limburgerhof; Norbert Goetz, Worms, all of Germany

[73] Assignee: BASF Aktiengesellschaft, Ludwigshafen, Germany

[21] Appl. No.: 97,116

[22] Filed: Jul. 27, 1993

[30] Foreign Application Priority Data

Jul. 29, 1992 [DE] Germany ............... 42 25 053.6

[51] Int. Cl.[6] .................................. C25B 3/02
[52] U.S. Cl. ............................. 204/78; 204/59 R
[58] Field of Search ..................... 204/78, 59 R

[56] References Cited

U.S. PATENT DOCUMENTS

| | | | |
|---|---|---|---|
| 3,254,093 | 5/1966 | Huisgen et al. | 260/295 |
| 4,284,825 | 8/1981 | Degner et al. | 204/59 R |
| 4,318,783 | 3/1982 | Buhmann et al. | 204/59 R |
| 4,845,096 | 7/1989 | Schlecker et al. | 514/233.5 |

FOREIGN PATENT DOCUMENTS

| | | |
|---|---|---|
| 284914 | 5/1988 | European Pat. Off. |
| 012240 | 6/1990 | European Pat. Off. |
| 378755 | 7/1990 | European Pat. Off. |

*Primary Examiner*—John Niebling
*Assistant Examiner*—Edna Wong
*Attorney, Agent, or Firm*—Keil & Weinkauf

[57] ABSTRACT

A process for preparing 4-dialkoxymethylpyrazoles of the formula I

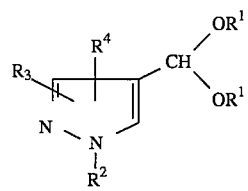

where
$R^1$ is n-alkyl,
$R^2$ is a hydrocarbon radical,
$R^3$ and $R^4$ are each hydrogen, a hydrocarbon radical, cyano, halogen or alkoxycarbonyl,
entails electrochemical oxidation of a 4-methylpyrazole of the formula II

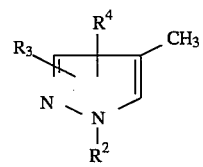

in the presence of an alkanol $R^1$—OH.

3 Claims, No Drawings

PREPARATION OF 4-DIALKOXYMETHYLPYRAZOLES

The present invention relates to a novel process for preparing 4-dialkoxymethylpyrazoles of the formula I

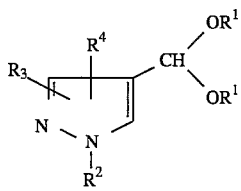

where
$R^1$ is n-alkyl,
$R^2$ is a hydrocarbon radical,
$R^3$ and $R^4$ are each hydrogen, a hydrocarbon radical, cyano, halogen or alkoxycarbonyl.

The pyrazoles I are used as intermediates for preparing crop protection agents and pharmaceuticals.

Some of the products of the process are known. They can be obtained as disclosed in U.S. Pat. No. 3,254,093 from 1,2,3-oxadiazoles which can be prepared only at great cost.

The electrochemical conversion of methyl-substituted isocyclic aromatic compounds into the corresponding acetals is described in EP-A 012,240.

It is an object of the present invention to prepare the pyrazoles I in a straightforward manner from readily obtainable starting compounds.

We have found that this object is achieved by a process for preparing the dialkoxymethylpyrazoles I which comprises electrochemical oxidation of a 4-methylpyrazole of the formula II

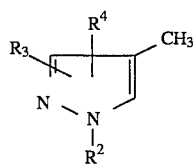

in the presence of an alkanol $R^1$—OH.

The process according to the invention can be illustrated as follows:

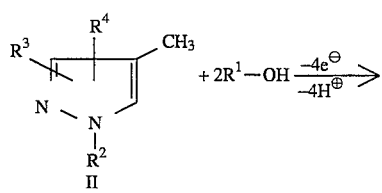

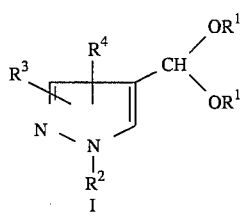

The starting compounds II which are not already known can be prepared by conventional methods, e.g. by reacting 1,3-diketo compounds with hydrazines (DE-A 29 22 591).

With a view to their use as intermediates for crop protection agents and pharmaceuticals, the preferred compounds I, and thus also the preferred starting compounds, are those where the substituents have the following meanings:

$R^1$
$C_1$–$C_6$-n-alkyl, preferably $C_1$–$C_4$-n-alkyl, especially methyl and ethyl;

$R^2$
$C_1$–$C_{12}$-alkyl, preferably $C_1$–$C_8$-alkyl, particularly methyl, ethyl, n-propyl, isopropyl, n-butyl, tert-butyl, n-pentyl, tert-amyl, n-hexyl, n-heptyl and n-octyl;

$C_3$–$C_{12}$-cycloalkyl, preferably $C_5$–$C_7$-cycloalkyl such as cyclopentyl, cyclohexyl and cycloheptyl;

unsubstituted or substituted phenyl such as phenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-methylphenyl, 3-methylphenyl, 4-methylphenyl, 2-methoxyphenyl, 3-methoxyphenyl, 4-methoxyphenyl, 2-ethoxyphenyl, 3-ethoxyphenyl, 4-ethoxyphenyl, 2-tert-butoxyphenyl, 3-tert-butoxyphenyl, 4-tert-butoxyphenyl, 2-methoxycarbonylphenyl, 3-methoxycarbonylphenyl, 4-methoxycarbonylphenyl, 2-ethoxycarbonylphenyl, 3-ethoxycarbonylphenyl, 4-ethoxycarbonylphenyl, 2-cyanophenyl, 3-cyanophenyl, 4-cyanophenyl, 2-methoxy-4-chlorophenyl, 2,4-dichlorophenyl, 3-methyl-6-chlorophenyl, 2,4,6-trichlorophenyl, 2-N-formylaminophenyl, 3-N-formylaminophenyl, 4-N-formylaminophenyl, 2-N-carboxymethylaminophenyl, 3-N-carboxymethylaminophenyl, 4-N-carboxymethylaminophenyl;

$R^3$ and $R^4$; additionally:
hydrogen;
cyano;
halogen such as fluorine, chlorine, bromine and iodine, preferably fluorine, chlorine and bromine;
alkoxycarbonyl-such as methoxycarbonyl, ethoxycarbonyl and tert-butoxycarbonyl.

It is additionally possible for the alkyl and cycloalkyl groups in $R^2$, $R^3$ and $R^4$ to have substituents, with $C_1$–$C_4$-alkyl, $C_1$–$C_4$-alkoxy, $C_1$–$C_5$-alkoxycarbonyl, hydroxyl and halogen being preferred.

The electrochemical oxidations can be carried out in divided but preferably in undivided flow cells.

The electrolyte is composed of the starting compound II and an alcohol $R^1$—OH and in a preferred embodiment, an auxiliary electrolyte is added to improve the conductivity. The electrolyte can contain a solvent which is inert under the electrolysis conditions, such as acetonitrile or methylene chloride; however, the electrolysis is preferably carried out without a solvent of this type.

The electrolyte preferably contains:

1–49, preferably 5–30, % by weight of the methylpyrazole II,

50–98.9, preferably 70–95, % by weight of the alcohol $R^1OH$ and 0.1–5, preferably 0.2–3, % by weight of the auxiliary electrolyte.

Suitable auxiliary electrolytes are salts, acids and bases. Examples of salts are fluorides such as potassium fluoride, sulfates such as tetramethylammonium methyl sulfate, tetrafluoroborates such as sodium tetrafluoroborate, and phosphates and phosphonates; sodium benzenesulfonate is preferred.

Examples of acids are sulfuric acid, alkyl- and arylsulfonic acids such as methylsulfonic acid and benzenesulfonic acid. Examples of suitable bases are alcoholates such as sodium methylate and hydroxides such as potassium hydroxide.

Suitable anode materials are noble metals such as platinum or oxides such as chromium oxide or ruthenium oxide, and mixed oxides such as $Ti/RuO_x$. However, graphite is the preferred anode material.

Suitable cathode materials are in general steel, iron, copper, tin, zinc, nickel and carbon, and noble metals such as platinum; however, graphite is preferred.

The electrolysis can be carried out batchwise or continuously, and it is possible if required to return unreacted starting material to the reaction.

The current density for the process according to the invention can be selected in the wide range from 0.1 to 25 $A/dm^2$, preferably from 1 to 10 $A/dm^2$. The oxidations are usually carried out at from 0° to 120° C., preferably from 20° to 80° C., generally under atmospheric pressure. However, it is also possible to operate under reduced pressure or, if low-boiling components are present, under elevated pressure. The amounts of charge are usually from 3.5 to 12, preferably from 4 to 8, F/mol of II.

The reaction solution is worked up by conventional methods, preferably distillation.

The process according to the invention converts the easily obtained 4-methylpyrazoles II into 4-dialkoxymethylpyrazoles I.

The acetals I can be hydrolyzed in a conventional manner to give the corresponding 4-formylpyrazoles III

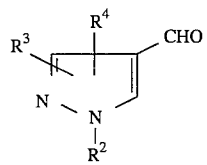

The compounds I therefore represent storage-stable protected forms of the considerably more sensitive aldehydes III.

The 4-formylpyrazoles III are used as precursors of crop protection agents (EP-A 378 755), of drugs (EP-A 284 914) or of optical brighteners (DE-A 17 70 614).

EXAMPLES

Example 1

Electrochemical synthesis of 4-dimethoxymethyl-1-phenylpyrazole
  Apparatus: undivided cell with 11 bipolar electrodes
  Anode: graphite
  Electrolyte: 80 g (506mmol) of 4-methyl-1-phenylpyrazole 30 g of sodium benzenesulfonate 2.89 kg of methanol
  Cathode: graphite
  Electrolysis temperature: 40° C.

The electrolysis was carried out with 5 F/mol of 4-methyl-1-phenylpyrazole. The electrolyte was passed through the cell at 200 l/h during the electrolysis. After the electrolysis was complete, the methanol was removed by distillation under atmospheric pressure, and the precipitated conducting salt was removed by filtration. Vacuum distillation yielded 50% of 4-dimethoxymethyl-1-phenylpyrazole which, with 86% conversion, corresponds to a yield based on reacted starting compound (selectivity) of 60%.

Example 2

Electrochemical synthesis of 1-(4-chlorophenyl)-4-dimethoxymethylpyrazole
  Apparatus: undivided cell with 11 bipolar electrodes
  Anode: graphite
  Electrolyte: 68 g (353 mmol) of 1-(4-chlorophenyl)-4-methylpyrazole 30 g of sodium benzenesulfonate 2.90 kg of methanol
  Cathode: graphite
  Electrolysis temperature: 30° C.

The electrolysis was carried out with 5.5 F/mol of 1-(4-chlorophenyl)-4-methylpyrazole. The electrolyte was passed through the cell at 200 l/h during the electrolysis. After working up as in Example 1, 50% of 1-(4-chlorophenyl)-4-dimethoxymethylpyrazole were isolated (selectivity 62%).

Example 3

Electrochemical synthesis of 1-(3-chlorophenyl)-4-dimethoxymethylpyrazole
  Apparatus: undivided cell with 9 bipolar electrodes
  Anode: graphite
  Electrolyte: 76 g (395 mmol) of 1-(3-chlorophenyl)-4-methylpyrazole 12 g of sodium benzenesulfonate 530 g of methanol
  Cathode: graphite
  Electrolysis temperature: 25° C.

The electrolysis was carried out with 6 F/mol of 1-(3-chlorophenyl)-4-methylpyrazole. The electrolyte was passed through the cell at 20 l/h during the electrolysis. After working up as in Example 1, 34% of 1-(3-chlorophenyl)-4-dimethoxymethylpyrazole were isolated (selectivity 40%).

Example 4

Electrochemical synthesis of 1-(2-chlorophenyl)-4-dimethoxymethylpyrazole
  Apparatus: undivided cell with 9 bipolar electrodes
  Anode: graphite
  Electrolyte: 102 g (530 mmol) of 1-(2-chlorophenyl)-4-methylpyrazole 14 g of sodium benzenesulfonate 600 g of methanol
  Cathode: graphite
  Electrolysis temperature: 20° C.

The electrolysis was carried out with 6 F/mol of 1-(2-chlorophenyl)-4-methylpyrazole. The electrolyte was passed through the cell at 20 l/h during the electrolysis. After working up as in Example 1, 40% of 1-(2-chlorophenyl)-4-dimethoxymethylpyrazole were isolated (selectivity 44%).

Example 5

Electrochemical synthesis of 4-dimethoxymethyl-1-methylpyrazole
  Apparatus: undivided cell with 9 bipolar electrodes
  Anode: graphite
  Electrolyte: 100 g (1.04 mmol) of 1,4-dimethylpyrazole 16 g of sodium benzenesulfonate 700 g of methanol
  Cathode: graphite
  Electrolysis temperature: 20° C.

The electrolysis was carried out with 7 F/mol of 1,4-dimethylpyrazole. The electrolyte was passed through the cell at 20 l/h during the electrolysis. After working up as in Example 1, 53% of 4-dimethoxymethyl-1-methylpyrazole were isolated (selectivity 58%).

We claim:

1. A process for preparing 4-dialkoxymethylpyrazoles of the formula I

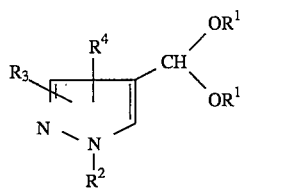

where
R$^1$ is n-alkyl,
R$^2$ is a hydrocarbon radical,
R$^3$ and R$^4$ are each hydrogen, a hydrocarbon radical, cyano, halogen or alkoxycarbonyl, which comprises electrochemical oxidation of a 4-methylpyrazole of the formula II

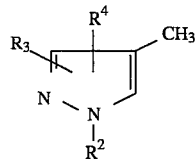

in the presence of an alkanol R$^1$—OH.

2. A process as claimed in claim 1, wherein the electrochemical oxidation is carried out in undivided flow cells.

3. A process as claimed in claim 1, wherein the electrochemical oxidation is carried out on graphite electrodes.

* * * * *